United States Patent
Smith et al.

(10) Patent No.: US 10,938,397 B2
(45) Date of Patent: Mar. 2, 2021

(54) RECORDING CHANNELS FOR BIOPOTENTIAL SIGNALS

(71) Applicant: University of Washington, Seattle, WA (US)

(72) Inventors: William Anthony Smith, Seattle, WA (US); Visvesh Sathe, Seattle, WA (US)

(73) Assignee: University of Washington, Seattle, WA (US)

( * ) Notice: Subject to any disclaimer, the term of this patent is extended or adjusted under 35 U.S.C. 154(b) by 61 days.

(21) Appl. No.: 16/347,541

(22) PCT Filed: Nov. 3, 2017

(86) PCT No.: PCT/US2017/059944
§ 371 (c)(1),
(2) Date: May 3, 2019

(87) PCT Pub. No.: WO2018/085664
PCT Pub. Date: May 11, 2018

(65) Prior Publication Data
US 2020/0266824 A1    Aug. 20, 2020

Related U.S. Application Data

(60) Provisional application No. 62/417,116, filed on Nov. 3, 2016.

(51) Int. Cl.
*H03M 1/00* (2006.01)
*A61B 5/0476* (2006.01)
(Continued)

(52) U.S. Cl.
CPC ............. *H03M 1/001* (2013.01); *A61B 5/04* (2013.01); *A61B 5/04004* (2013.01);
(Continued)

(58) Field of Classification Search
CPC .... H03M 1/001; A61B 5/0478; A61B 5/0476; A61B 5/7203; A61B 5/04;
(Continued)

(56) References Cited

U.S. PATENT DOCUMENTS

| 3,656,065 A | 4/1972 | Reinhard et al. |
| 4,574,250 A | 3/1986 | Senderowicz |

(Continued)

FOREIGN PATENT DOCUMENTS

| EP | 0301790 A2 | 2/1989 |
| EP | 2904963 A1 | 8/2015 |
| WO | 2018085664 A1 | 5/2018 |

OTHER PUBLICATIONS

International Search Report and Written Opinion dated Jan. 17, 2018, for PCT Application No. PCT/US17/59944, 12 pages.
(Continued)

*Primary Examiner* — Khai M Nguyen
(74) *Attorney, Agent, or Firm* — Dorsey & Whitney LLP

(57) ABSTRACT

Examples of recording channels and methods for biopotential signal acquisition and/or recording are described. Recording channels described herein may implement any combination of techniques described herein including multiplexing of multiple electrode inputs, delta encoding of biopotential signals, and common mode suppression.

14 Claims, 7 Drawing Sheets

(51) Int. Cl.
  *A61B 5/00* (2006.01)
  *A61B 5/04* (2006.01)
  *A61N 1/36* (2006.01)
  *A61N 1/00* (2006.01)
  *A61B 5/0478* (2006.01)

(52) U.S. Cl.
  CPC .......... *A61B 5/0476* (2013.01); *A61B 5/4064* (2013.01); *A61B 5/7203* (2013.01); *A61B 5/7225* (2013.01); *A61N 1/00* (2013.01); *A61N 1/3606* (2013.01); *A61N 1/36135* (2013.01); *A61B 5/0478* (2013.01)

(58) Field of Classification Search
  CPC . A61B 5/04004; A61B 5/4064; A61B 5/7225; A61N 1/00; A61N 1/3606; A61N 1/36135
  USPC ........................................ 341/141, 143, 155
  See application file for complete search history.

(56) References Cited

U.S. PATENT DOCUMENTS

| | | | |
|---|---|---|---|
| 5,142,238 A | 8/1992 | White | |
| 5,703,589 A | 12/1997 | Kalthoff et al. | |
| 6,140,950 A | 10/2000 | Oprescu | |
| 6,437,720 B1 | 8/2002 | Yin et al. | |
| 7,864,088 B2 * | 1/2011 | Teo ..................... | H03M 1/1019 341/118 |
| 7,896,807 B2 | 3/2011 | Clancy et al. | |
| 7,903,010 B1 * | 3/2011 | Melanson ............ | H03M 3/474 341/143 |
| 2003/0197636 A1 | 10/2003 | Confalonieri et al. | |
| 2005/0215916 A1 | 9/2005 | Fadem et al. | |
| 2006/0173364 A1 | 8/2006 | Clancy et al. | |
| 2007/0120715 A1 | 5/2007 | Zierhofer | |
| 2015/0223710 A1 | 8/2015 | Cong et al. | |

OTHER PUBLICATIONS

Chen, et al., "A Fully Integrated 8-Channel Closed-Loop Neural-Prosthetic CMOS SoC for Real-Time Epileptic Seizure Control", IEEE Journal of Solid-State Circuits, vol. 49, No. 1, pp. 232-247, Jan. 2014.
Mendrela, et al., "A Bidirectional Neural Interface Circuit With Active Stimulation Artifact Cancellation and Cross-Channel Common-Mode Noise Suppression", IEEE Journal of Solid-State Circuits, vol. 51, Issue 4, Apr. 2016.
Muller, et al., "A Minimally Invasive 64-Channel Wireless μECoG Implant", IEEE Journal of Solid-State Circuits, vol. 50, No. 1, pp. 1-16, Jan. 2015.
Song, et al., "Fully Integrated Biopotential Acquisition Analog Front-End IC", Sensors 2015, 15, 25139-25156; doi:10.3390/s151025139, ISSN 1424-8220, pp. 25139-25156, Sep. 2015.
International Preliminary Report on Patentability dated May 16, 2019, for PCT Application No. PCT/US2017/059944, 6 pages.
Abo, et al., A 1.5-V, 10-BIT, 14.3-MS/S CMOS Pipeline Analog-To-Digital Converter, IEEE Journal of Solid-State Circuits, vol. 34, No. 5, May 1999, 8 pages.
Aziz, et al., 256-Channel Neural Recording and Delta Compression Microsystem With 3D Electrodes, IEEE Journal of Solid-State Circuits, vol. 44, No. 3, Mar. 2009, 11 pages.
Benabid, Deep Brain Stimulation for Parkinson's Disease, Current Opinion in Neurobiology, Dec. 2003, 11 pages.
Biederman, et al., A 4.78 mm2 Fully-Integrated Neuromodulation SoC Combining 64 Acquisition Channels With Digital Compression and Simultaneous Dual Stimulation, IEEE Journal of Solid-State Circuits, vol. 50, No. 4, Apr. 2015, 10 pages.
Chen, et al., A 24 W 11-bit 1-MS/s SAR ADC With a Bidirectional Single-side Switching Technique, IEEE, Sep. 2014, 4 pages.
Chen, et al., A Fully Integrated 8-Channel Closed-Loop Neural-Prosthetic CMOS SoC for Real-Time Epileptic Seizure Control, IEEE Journal of Solid-State Circuits, vol. 49, No. 1, Jan. 2014, 16 pages.
Denison, et al., Chopper-Stabilized Instrumentation Amplifier for Chronic Measurement of Neural Field Potentials, IEEE Journal of Solid-State Circuits, vol. 42, No. 12, Dec. 2007, 12 pages.
Enz, et al., Circuit Techniques for Reducing the Effects of Op-Amp Imperfections: Autozeroing, Correlated Double Sampling, and Chopper Stabilization, Proceedings of the IEEE, vol. 84, No. 11, Nov. 1996, 31 pages.
Franks, et al., Impedance Characterization and Modeling of Electrodes for Biomedical Applications, IEEE Transactions on Biomedical Engineering, vol. 52, No. 7, Jul. 2005, 8 pages.
Gao, et al., HermesE: A 96-Channel Full Data Rate Direct Neural Interface in 0.13 m CMOS, IEEE Journal of Solid-State Circuits, vol. 47, No. 4, Apr. 2012, 13 pages.
Gnadt, et al., Spectral Cancellation of Microstimulation Artifact for Simultaneous Neural Recording In Situ, IEEE Transactions on Biomedical Engineering, vol. 50, No. 10, Oct. 2003, 7 pages.
Goes, et al., Low-Power Low-Voltage CMOS A/D Sigma-Delta Modulator for Bio-Potential Signals Driven by a Single-Phase Scheme, IEEE Transactions on Circuits and Systems—I: Regular Papers, vol. 52, No. 12, Dec. 2005, 10 pages.
Harpe, et al., A 26 W 8 bit 10 MS/s asynchronous SAR ADC for low energy radios, IEEE Journal of Solid-State Circuits, Aug. 2011, 12 pages.
Hashimoto, et al., A template subtraction method for stimulus artifact removal in high-frequency deep brain stimulation, Journal of Neuroscience Methods, Jan. 2002, 6 pages.
Holtzheimer, et al., Deep Brain Stimulation for Psychiatric Disorders, Author manuscript available in PMC, Apr. 2015, 22 pages.
Kim, et al., Preliminary Study of the Thermal Impact of a Microelectrode Array Implanted in the Brain, Proceedings of the 28th IEEE EMBS Annual International Conference, Sep. 2006, 4 pages.
Limnuson, et al., Real-Time Stimulus Artifact Rejection Via Template Subtraction, IEEE Transactions on Biomedical Circuits and Systems, vol. 8, No. 3, Jun. 2014, 10 pages.
Liu, et al., A 10-bit 50-MS/s SAR ADC With a Monotonic Capacitor Switching Procedure, IEEE Journal of Solid-State Circuits, vol. 45, No. 4, Apr. 2010, 10 pages.
McPherson, et al., Targeted, activity-dependent spinal stimulation produces long-lasting motor recovery in chronic cervical spinal cord injury, PNAS, Sep. 2015, 6 pages.
Mendrela, et al., A Bidirectional Neural Interface Circuit With Active Stimulation Artifact Cancellation and Cross-Channel Common-Mode Noise Suppression, IEEE Journal of Solid-State Circuits, vol. 51, No. 4, Apr. 2016.
Mendrela, et al., Enabling Closed-Loop Neural Interface: A Bi-Directional Interface Circuit with Stimulation Artifact Cancellation and Cross-Channel CM Noise Suppression, Symposium on VLSI Circuits Digest of Technical Papers, Jun. 2015, 2 pages.
Miller, et al., Power-Law Scaling in the Brain Surface Electric Potential, PLoS Computational Biology, vol. 5, Issue 12, Dec. 2009, 10 pages.
Miranda, et al., DARPA-funded efforts in the development of novel brain-computer interface technologies, Journal of Neuroscience Methods, Aug. 2014, 16 pages.
Mirzaei, et al., Analysis of First-Order Anti-Aliasing Integration Sampler, IEEE Transactions on Circuits and Systems—I: Regular Papers, vol. 55, No. 10, Nov. 2008, 12 pages.
Moritz, et al., Direct control of paralysed muscles by cortical neurons, Nature, vol. 456, Dec. 2008, 5 pages.
Muller, et al., A Miniaturized 64-Channel 225μW Wireless Electrocorticographic Neural Sensor, IEEE International Solid-State Circuits Conference, Feb. 2014, 3 pages.
Muller, et al., A Minimally Invasive 64-Channel Wireless ECoG Implant, IEEE Journal of Solid-State Circuits, vol. 50, No. 1, Jan. 2015, 16 pages.
Ng, et al., A Multi-Channel Neural-Recording Amplifier System with 90dB CMRR Employing CMOS-Inverter-Based OTAs with CMFB Through Supply Rails in 65nm CMOS, IEEE International Solid-State Circuits Conference, Feb. 2015, 3 pages.

(56) References Cited

OTHER PUBLICATIONS

Pepin, et al., A High-Voltage Compliant, Electrode-Invariant Neural Stimulator Front-End in 65nm Bulk-CMOS, IEEE, Sep. 2016, 4 pages.

Raducanu, et al., Time multiplexed active neural probe with 678 parallel recording sites, IEEE, Sep. 2016, 4 pages.

Schreier, et al., Delta-Sigma Modulators Employing Continuous-Time Circuitry, EEE Transactions on Circuits and Systems—I: Fundamental Theory and Applications, vol. 43, No. 4, Apr. 1996, 9 pages.

Sharma, et al., Noise and Impedance of the SIROF Utah Electrode Array, IEEE, Nov. 2016, 3 pages.

Smith, et al., A Scalable, Highly-Multiplexed Delta-Encoded Digital Feedback ECoG Recording Amplifier with Common and Differential-Mode Artifact Suppression, IEEE, Jun. 2017, 2 pages.

Smith, et al., A Spectrum-Equalizing Analog Front End for Low-Power Electrocorticography Recording, IEEE, Sep. 2014, 4 pages.

Smith, et al., Exploiting Electrocorticographic Spectral Characteristics for Optimized Signal Chain Design: A 1.08 W Analog Front End With Reduced ADC Resolution Requirements, IEEE Transactions on Biomedical Circuits and Systems, vol. 10, No. 6, Dec. 2016, 10 pages.

Sun, et al., Responsive Cortical Stimulation for the Treatment of Epilepsy, Neurotherapeutics: The Journal of the American Society for Experimental NeuroTherapeutics, Jan. 2008, 7 pages.

Talwalkar, et al., Integrated CMOS Transmit-Receive Switch Using LC-Tuned Substrate Bias for 2.4-GHz and 5.2-GHz Applications, IEEE Journal of Solid-State Circuits, vol. 39, No. 6, Jun. 2004.

Tomovich, Circuits with Quantized Feedback, IRE Transactions—Circuits Theory, Jun. 1955, 5 pages.

Wagenaar, et al., Real-time multi-channel stimulus artifact suppression by local curve fitting, Journal of Neuroscience Methods, May 2002, 8 pages.

Xu, et al., A 15-Channel Digital Active Electrode System for Multi-Parameter Biopotential Measurement, IEEE Journal of Solid-State Circuits, vol. 50, No. 9, Sep. 2015.

* cited by examiner

RECORDING CHANNELS FOR BIOPOTENTIAL SIGNALS

CROSS-REFERENCE TO RELATED APPLICATION(S)

This application is a 35 U.S.C. § 371 National Stage Application of PCT Application No. PCT/US2017/059944, filed Nov. 3, 2017, which claims the benefit under 35 U.S.C. § 119 of the earlier filing date of U.S. Provisional Application Ser. No. 62/417,116 filed Nov. 3, 2016, the entire contents of which are hereby incorporated by reference, in their entirety, for any purposes.

STATEMENT REGARDING RESEARCH & DEVELOPMENT

This invention was made with government support under Grant No. EEC1028725, awarded by the National Science Foundation (NSF). The government has certain rights in the invention.

TECHNICAL FIELD

Embodiments described herein relate to electronics, circuits, systems, and methods which may be useful for biopotential signal processing, such as in neural signal processing.

BACKGROUND

Bidirectional Brain-Computer Interfaces (BBCIs) generally refer to electronic systems that may allow computers to simultaneously record, process, and stimulate neural activity. These systems may facilitate scientific inquiry into human brain function and are ushering in a new era of neuroprosthetics. These advances have the potential to enable new treatments for a number of neurological disorders including Parkinson's Disease, epilepsy, and depression. Simultaneously, BBCI research continues to drive progress in the field of human-computer interaction.

SUMMARY

Figure 1:
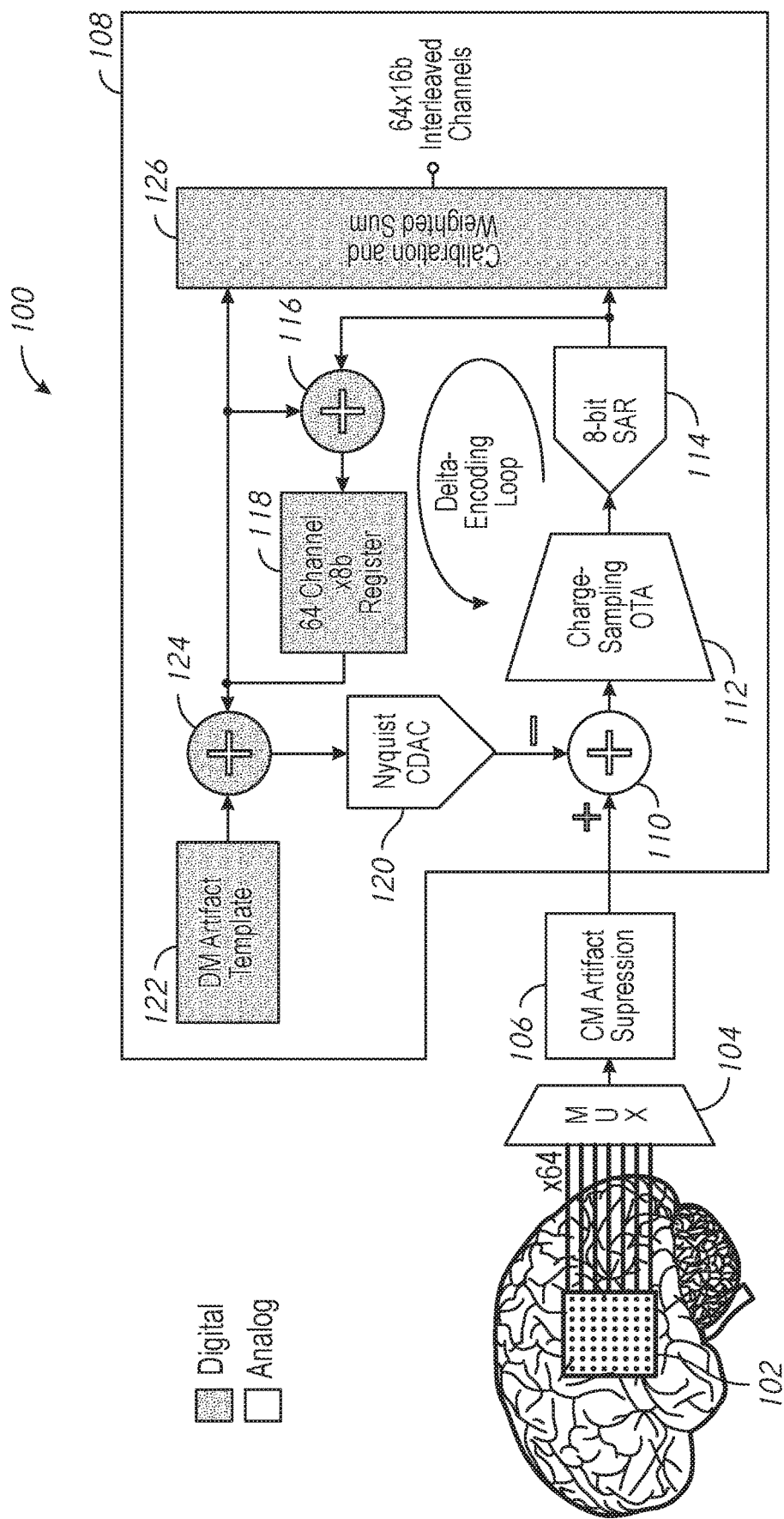
FIG. 1 is a schematic illustration of recording channel(s) in accordance with examples described herein.

Examples of encoding circuitry are described herein. In some examples, encoding circuitry may include a first combiner configured to receive an analog input signal and an analog feedback signal. The first combiner may be configured to combine the analog input signal with the analog feedback signal to provide an analog difference signal. The encoding circuitry may further include an amplifier configured to receive the analog difference signal and amplify the analog difference signal to provide an amplified analog difference signal. The encoding circuitry may further include an analog-to-digital converter configured to convert the amplified analog difference signal into a digital difference signal. The encoding circuitry may further include an accumulator configured to accumulate the digital difference signal to provide an accumulated digital difference signal. The encoding circuitry may further include a digital-to-analog converter configured to convert the digital difference signal into the analog feedback signal. The encoding circuitry may further include a multiplier configured to provide a multiplied accumulated digital difference signal. The encoding circuitry may further include a second combiner configured to combine the multiplied accumulated digital difference signal and the digital difference signal to provide a digital output signal.

In some examples, the digital-to-analog converter has a bit resolution less than a bit precision of the digital output signal.

In some examples, the analog-to-digital converter has a bit resolution less than a bit precision of the digital output signal.

In some examples, the digital-to-analog converter and the analog-to-digital converter have bit resolutions less than a bit precision of the digital output signal. In some examples, the digital-to-analog converter and the analog-to-digital converter each have an 8-bit resolution, and the digital output signal has a 14 bit precision.

In some examples, a first dynamic range of the amplifier is less than a second dynamic range of the digital output signal.

In some examples, the analog input signal comprises a biopotential signal.

Examples of multiplexed signal encoders are described herein. In some examples, a multiplexed signal encoder includes a plurality of electrodes, a multiplexer coupled to the plurality of electrodes and configured to sequentially output analog signals received from each of the plurality of electrodes, and a delta-encoder coupled to the multiplexer, the delta-encoder configured to encode the analog signals sequentially output from the multiplexer by combining the analog signals with respective feedback signals based on a previous value of the analog signals. The delta-encoder may include a register configured to store respective previous values of the analog signals, and a controller configured to output selected previous values from the register to correspond with the sequentially output analog signals.

In some examples, the analog signals comprise biopotential signals.

In some examples, the delta-encoder includes an amplifier, and the amplifier is configured to amplify analog signals received from each of the plurality of electrodes.

In some examples, the delta-encoder includes a combiner configured to receive the analog signals and respective analog feedback signals, the combiner configured to combine the analog signals with the respective analog feedback signals to provide analog difference signals. In some examples, the delta-encoder includes an amplifier configured to receive the analog difference signals and amplify the analog difference signals to provide amplified analog difference signals. In some examples, the delta-encoder includes an analog-to-digital converter configured to convert the amplified analog difference signals into digital difference signals. In some examples, the delta-encoder includes an accumulator configured to accumulate the digital difference signals to provide accumulated digital difference signals. The register may be configured to store the accumulated digital difference signals indicative of the previous values of the analog signals. In some examples, the delta-encoder includes a digital-to-analog converter configured to convert the digital difference signals into the analog feedback signals.

In some examples, the delta-encoder may further include a multiplier configured to provide multiplied accumulated digital difference signals, and another combiner configured to combine the multiplied accumulated digital difference signals and the digital difference signals to provide digital output signals.

In some examples, the digital-to-analog converter and the analog-to-digital converter have bit resolutions less than a bit precision of the digital output signals.

In some examples, a first dynamic range of the amplifier is less than a second dynamic range of the digital output signals.

Examples of methods are described herein. An example method may include a method for encoding differential signals received from a pair of electrodes. The method may include charging input capacitors coupled to the pair of electrodes to a reference value, coupling the input capacitors to the pair of electrodes, disconnecting the input capacitors from the pair of electrodes, coupling the input capacitors together to provide a common mode value on the input capacitors, coupling the pair of electrodes to the input capacitors having the common mode value to provide a differential output signal, and encoding the differential output signal to provide a digital output signal.

In some examples, the differential signals comprise biopotential signals.

In some examples, encoding the differential output signals comprises delta-encoding the differential output signals.

In some examples, the method further includes multiplexing the input capacitors between a plurality of pairs of electrodes.

In some examples, prior to connecting the input capacitors to a next pair of electrodes, the method may further include charging the input capacitors to the reference value, coupling the input capacitors to the next pair of electrodes, disconnecting the input capacitors from the next pair of electrodes, and coupling the input capacitors together to provide another common mode value on the input capacitors.

In some examples, charging the input capacitors to the reference value may include closing a first set of switches between one side of the input capacitors and a first reference value, and closing a second set of switches between a second side of the input capacitors and a second reference value. In some examples, coupling the input capacitors to the pair of electrodes may include closing a third set of switches between the second side of the input capacitors and the pair of electrodes and opening the second set of switches. In some examples, disconnecting the input capacitors from the pair of electrodes may include opening the third set of switches. In some examples, coupling the input capacitors together may include closing a fourth switch coupled between the input capacitors. In some examples, coupling the pair of electrodes to the input capacitors may include opening the fourth switch and closing the third set of switches.

DETAILED DESCRIPTION

Certain details are set forth herein to provide an understanding of described embodiments of technology. However, other examples may be practiced without various of these particular details. In some instances, well-known circuits, control signals, timing protocols, software operations, and/or biological stimulator components have not been shown in detail in order to avoid unnecessarily obscuring the described embodiments. Other embodiments may be utilized, and other changes may be made, without departing from the spirit or scope of the subject matter presented here.

Examples described herein may provide a scalable, time-division multiplexed biopotential recording front-end which may be capable of real-time differential- and common-mode artifact suppression. Examples of a delta-encoded recording architecture is described which may use a low-noise amplifier, an analog-to-digital converter (ADC) having a particular bit resolution (e.g., an 8-bit ADC), and a digital-to-analog converter (DAC) having a particular bit resolution (e.g., an 8-bit DAC) to achieve an effective bit resolution at an output which is greater than the bit resolution of the ADC and/or DAC (e.g., an effective 14-bit precision). The digital feedback architecture may in some examples be leveraged to time-division multiplex multiple (e.g., 64) differential input channels onto a shared mixed-signal front-end. The time-division multiplexing in some examples may reduce channel area (e.g., by 10× compared designs where multiplexing as described herein may not be used). The input DAC may be overloaded with differential artifact suppression and may work together with a switched-capacitor common-mode suppression technique in some examples.

BBCI applications, which may chronic (e.g., long-term) BBCI applications, face several engineering challenges. The desire for high electrode density and large spatial coverage motivates neural interfaces with many (e.g., thousands) electrodes; however, the silicon area required to scale existing solutions may be prohibitive. Concurrent stimulation and recording activity resulting from closed-loop neuromodulation may generate large stimulation artifacts that may obfuscate important signals during and shortly after stimulation. Moreover, power density requirements due to tissue heating remain restrictive, particularly in monolithic solutions. Additionally, a single-chip solution with efficient operation for both electrocorticography (ECoG) (e.g., <500 Hz signals) and single neuron recording (e.g., <8 kHz signals) may be desired.

Examples described herein may provide a channel-, process-, and frequency-scalable recording system which may be manufactured in a standard CMOS process (e.g., a 65 nm process). Examples described herein may provide time-domain multiplexed recording channels, which may facilitate a reduction in silicon area needed for the recording channels (e.g., a tenfold reduction). Examples described herein may utilize a delta-encoded feedback loop, which may exploit biopotential signal (e.g., neural signal) statistics to provide large dynamic range while utilizing low-precision data converters to achieve high-precision recording. Examples described herein may provide real-time common- and differential-mode artifact suppression at amplifier inputs. Examples described herein may scale efficiently in frequency and channel-count, making examples useful for a variety of biopotential acquisition and/or stimulation applications.

FIG. 1 is a schematic illustration of recording channel(s) in accordance with examples described herein. The recording channel(s) 100 include electrodes 102, multiplexer 104, common mode suppression circuitry 106, and delta encoder 108. The delta encoder 108 may include combiner 110, amplifier 112, analog-to-digital converter 114, accumulator 116, register 118, and digital-to-analog converter 120. In some examples, the delta encoder 108 may include differential mode artifact suppression circuitry 122 and combiner 124. The recording channel(s) 100 may include combiner 126 which may provide output signals. Additional, fewer, and/or different components may be used in other examples. Recording channels described herein, such as recording channel(s) 100 may form all or part of a neural recording system for recording biopotential signals.

Accordingly, the recording channel(s) 100 of FIG. 1 may implement three techniques described herein: (1) multiplexing of multiple electrode inputs; (2) delta encoding of biopotential signals; and (3) common mode suppression. While the recording channel(s) 100 of FIG. 1 may implement all three techniques, in some examples, recording channel(s) may be provided which implement one or two of the described techniques. Accordingly, components used to implement certain of the techniques may not be present in all examples. An overview of each technique, and examples of components used to implement each technique, is provided herein and examples are described with reference to FIG. 1.

Examples of systems and recording channels described herein may utilize delta encoding (e.g., may include one or more delta encoders), such as delta encoder 108 of FIG. 1. Generally, delta encoding described herein may include a feedback path utilizing digital signals. In some examples, delta encoders described herein may advantageously allow for the use of an analog-to-digital converter and a digital-to-analog converter having a certain bit resolution, while the delta encoder itself provides output signals having a different, greater, bit precision (e.g., output signal bit resolution). Moreover, delta encoders described herein may advantageously allow for the use of an amplifier having a dynamic range less than a dynamic range of the output signals provided by the delta encoder.

The delta encoder 108 may include combiner 110, amplifier 112, analog-to-digital converter 114, accumulator 116, and digital-to-analog converter 120. During operation, the combiner 110 may receive an analog input signal (e.g., from the electrodes 102 and/or through intermediate components, such as multiplexer 104 in some examples). The analog input signal may be a biopotential signal (e.g., a signal derived from a biological process and/or tissue). Examples of biopotential signals include, but are not limited to, neural signals, including neural signals from the brain (e.g., electrocorticography signals) and/or spinal system. The biopotential signals may refer to any of a variety of electrical signals obtained from a biological source—e.g., voltage signal, current signal, capacitance signal, etc.

Any number of electrodes 102 may be used—including 64 electrodes in the example of FIG. 1. Other numbers of electrodes are possible, such as 2, 4, 8, 16, 32, 128, 256, 1028, or another number of electrodes. The electrodes 102 may be in electrical communication with one or more neurons and/or other biopotential signal generators. For example, electrodes 102 may be implanted and/or otherwise in electrical communication with brain, nerve, muscle, or other tissue. The electrodes 102 in some examples may be provided in the form of one or more arrays.

The combiner 110 may be implemented using an adder in some examples. Other combinations are possible in other examples. The combiner 110 may combine the analog input signal with an analog feedback signal provided by a feedback path of the delta encoder 108. The combiner 110 may provide an analog difference signal indicative of the combination of the analog input signal and the analog feedback signal. The analog input signal may be provided at a positive input of the combiner 110 while the analog feedback signal may be provided at a negative input of the combiner 110. Accordingly, in some examples, the combiner 110 may subtract the analog feedback signal from the analog input signal to provide the analog feedback signal.

Delta encoders described herein may include one or more amplifiers, such as amplifier 112 of delta encoder 108 in FIG. 1. The amplifier 112 may be coupled to the combiner 110. The amplifier 112 may receive at its input the analog difference signal provided by the combiner 110. The amplifier 112 may amplify the analog difference signal. The amplifier 112 may have a particular dynamic range. The dynamic range of amplifier 112 may in some examples be less than a dynamic range of an output of the delta encoder 108 itself. The amplifier 112 may be implemented using, for example, a low noise amplifier, an operational transconductance amplifier (OTA), a charge-sampling OTA, and/or combinations thereof. Other amplifier configurations may be used in other examples. The amplifier 112 may amplify the analog difference signal provided by the combiner 110 to provide an amplified analog difference signal.

Delta encoders described herein may include one or more analog-to-digital converters, such as analog-to-digital converter 114 of delta encoder 108 in FIG. 1. The analog-to-digital converter 114 may be implemented using, for example, a successive approximation ADC. Other analog-to-digital converter designs may be used in other examples. The analog-to-digital converter 114 may be coupled to the amplifier 112 and may convert the amplified analog difference signal into a digital difference signal The analog-to-digital converter 114 may have a particular bit resolution, such as an 8-bit resolution as shown in FIG. 1. Other bit resolutions may be used in other examples, including 4-bit resolution, 16-bit resolution, or other bit resolutions. The bit resolution of the ADC generally refers to the number of discrete values that may be provided by the ADC over a range of input analog values. Generally, an ADC having an n-bit resolution may encode an analog input into $2^n$ levels— e.g., an 8-bit ADC may encode an analog input into 256 levels. Generally, as described herein, a bit resolution of the ADC used in delta encoders described herein (e.g., delta encoder 108) may be less than a bit precision or bit resolution of the output signals provided by the recording channel (e.g., at an output of combiner 126 in FIG. 1).

Delta encoders described herein may include one or more accumulators, such as accumulator 116 of delta encoder 108 in FIG. 1. The accumulator 116 may receive the digital difference signal from the analog-to-digital converter 114 and may accumulate the digital difference signal to provide an accumulated digital difference signal. Generally, the accumulator 116 may track a large-scale variation of the input signal based on incremental changes received from the analog-to-digital converter 114. The accumulator 116 may be implemented using accumulator circuitry.

Delta encoders described herein may include one or more digital-to-analog converters, such as digital-to-analog converter 120 of FIG. 1. The digital-to-analog converter 120 may be implemented using, for example, a control digital-to-analog converter (CDAC). Other digital-to-analog converter designs may be used in other examples. The digital-to-analog converter 120 may operate at a Nyquist rate. The digital-to-analog converter 120 may be coupled to the accumulator 116 and may convert the accumulated digital difference signal into the analog feedback signal. The digital-to-analog converter 120 may have a particular bit resolution, such as an 8-bit resolution as shown in FIG. 1. Other bit resolutions may be used in other examples, including 4-bit resolution, 16-bit resolution, or other bit resolutions. The bit resolution of the DAC generally refers to the number of discrete values that may be accepted by the DAC and converted to a range of input analog values. Generally, a DAC having an n-bit resolution may receive a digital input from $2^n$ levels—e.g., an 8-bit DAC may receive a digital input having 256 levels. Generally, as described herein, a bit resolution of the DAC used in delta encoders described herein (e.g., delta encoder 108) may be less than a bit precision or bit resolution of the output signals provided by the recording channel (e.g., at an output of combiner 126 in FIG. 1). The bit resolution of the digital-to-analog converter 120 may be the same as a bit resolution of the analog-to-digital converter 114 in some examples. In some examples, the bit resolution of the digital-to-analog converter 120 may be different than the bit resolution of the analog-to-digital converter 114. The bit resolution of both the analog-to-digital converter 114 and the digital-to-analog converter 120 may be less than a bit resolution (e.g., bit precision) of the output signals provided by the recording channel.

For example, the ADC and DAC utilized in delta encoders described herein may have overlapping resolutions that are based at least in part on the gain of the feedforward path of the delta encoder. For example, if the forward gain is 1000, the ADC least significant bit (LSB) at the output may become 1000 times smaller at the amplifier input. The ADC LSB voltage amplitude at the input compared to the DAC LSB voltage amplitude may in part determine the amount of overlap between the two ranges. Accordingly, the range of voltages covered by the encoder system may be from ADC_LSB/sqrt(12) to DAC_MSB/sqrt(2) (RMS voltage). This range may be considerably larger (e.g. 14 bits) than the individual ranges of the converters, at least in part because they have a relatively small overlap (e.g., a couple of bits).

In this manner, the analog feedback signal provided by the digital-to-analog converter 120 may represent a coarse approximation of a previous value of the analog input signal. In this manner the analog difference signal generated by combining (e.g., subtracting) the analog input signal with the analog feedback signal may represent a difference between successive values of the input signal. Accordingly, consider biopotential signals input to the delta encoder 108. Biopotential signals may generally be characterized in that they may have a relatively large amplitude, low frequency component and a relatively small amplitude, high frequency component, both of which may be desired to be accurately interpreted by the recording channel. The delta encoder 108 generally allows for feedback based on the difference between successive samples of the input signal. In the case of the large amplitude, low frequency component, the difference between successive samples may be small, at least because the variation is of a low frequency (e.g., slow varying). In the case of the small amplitude, high frequency component, the difference between successive samples may again be small, at least because the amplitude of this signal component is small, although it may be fast-varying (e.g., high frequency). Accordingly, components of the delta encoder 108 may not need to accommodate the entire dynamic range of the input (or output) signals, and instead may have an available dynamic range based on the difference between successive samples of the input signal. Accordingly, the amplifier 112, analog-to-digital converter 114, and digital-to-analog converter 120 may have properties (e.g., dynamic range, bit resolution) sufficient for the expected variation in the difference signal, rather than the expected variation in the input (or output) signal.

Examples of delta encoders described herein may include an output combiner, such as combiner 126 of the delta encoder 108 in FIG. 1. The combiner 126 may be coupled to the analog-to-digital converter 114 and the accumulator 116. The combiner 126 may combine (e.g., sum) the digital difference signal provided by the analog-to-digital converter 114 with the accumulated digital difference signal provided by the accumulator 116 to provide a digital output signal indicative of the analog input signal. Note that a bit precision (e.g., bit resolution) of the output signal may be greater than a bit resolution of the analog-to-digital converter 114 and/or digital-to-analog converter 120. The accumulator 116 may advantageously accumulate successive changes to the input signal such that an output of the accumulator 116 may correspond with a previous value of the input signal, which may boost the bit precision of the output signal. In some examples, the combiner 126 may include a multiplier which may be used to weight the accumulated digital difference signal and/or the digital difference signal. Weighting one or both of these signals may compensate for non-idealities in the recording channel, such as nonidealities in the digital-to-analog converter 120.

Examples of recording channels described herein may utilize multiplexing (e.g., time division multiplexing). Components which may be used to implement multiplexing include, referring to FIG. 1, multiplexer 104 and register 118. Note that multiplexing techniques described herein may be used whether or not delta encoding techniques are used. For example, the multiplexer 104 and register 118 and multiplexing techniques described herein may be used with or without delta encoder 108 (e.g., a different encoder may be used in other examples).

The multiplexer 104 may be coupled to the electrodes 102 and may sequentially output analog signals from each of the electrodes 102. Accordingly, in the example of FIG. 1, 64 signals (e.g., one from each of the electrodes 102) may be provided to an input of multiplexer 104. The multiplexer 104 may output each of those signals, one at a time. The frequency of the multiplexer switching between signals may vary in some examples. The multiplexer 104 may be controlled by a controller (e.g., one or more processors, microcontrollers, and/or control logic), not shown in FIG. 1.

The sequentially output signals from the multiplexer 104 may be provided to an encoder (e.g., the delta encoder 108 at the combiner 110). In this manner, the encoder may be shared among all the electrodes 102. For example, the delta encoder 108 may encode signals received from each of the electrodes 102. Note that this allows the amplifier 112, analog-to-digital converter 114, and/or digital-to-analog converter 120 to be shared and used to encode signals from multiple (e.g., all) of the electrodes 102. Sharing encoders and/or components of encoders may decrease an amount of area on an electronics chip and/or board required to implement the recording channel(s) 100.

In some examples, to facilitate an encoder encoding signals from time-multiplexed electrodes, components may be used to ensure that a feedback signal in the encoder pertains to the same electrode as is received at the input. For example, referring to FIG. 1, the delta encoder 108 may include register 118. The register 118 may store accumulated digital difference signals received from the accumulator 116. The register 118 may sequentially output accumulated digital difference signals from the register 118 in synchronization with the sequentially output analog input signals provided by the multiplexer 104. In this manner, the register 118 may output an accumulated digital difference signal indicative of a last value associated with a same electrode as being provided to the input combiner 110. Accordingly, by storing values for each of electrodes 102 in the register 118, the delta encoder 108 may be used to encode signals from all electrodes 102 in a time multiplexed manner.

The register 118 may be implemented using generally any electronic storage including, but not limited to, one or more registers, flip-flops, memory, flash, RAM, ROM, or combinations thereof. The register 118 may be controlled by a controller (e.g., one or more processors, microcontrollers, and/or control logic), not shown in FIG. 1. A frequency of different outputs of the register 118 may correspond with a frequency of switching of the multiplexer 104. The register 118 may have a capacity corresponding to the number of electrodes 102 and an expected number of bits in the accumulated digital difference signal. In the example of FIG. 1, the register 118 may have 64 channels (one channel per electrode of electrodes 102), with 8 bits of storage per channel.

Accordingly, combiner 126 may output signals representing encoded values from each of the electrodes 102 in a time multiplexed manner. As shown in FIG. 1, the combiner 126 may output 64 channels, corresponding to the 64 electrodes of electrodes 102. In some examples, the encoded signal for each channel may be 16 bits as shown in FIG. 1. Note that, due to the operation of the delta encoder 108 described herein, the analog-to-digital converter 114 may have an 8-bit resolution, the digital-to-analog converter 120 may have an 8-bit resolution, yet the combiner 126 may provide 16-bit signals.

Examples of recording channels described herein may utilize artifact suppression (e.g., common mode suppression and/or differential mode suppression). Components which may be used to implement artifact suppression include, referring to FIG. 1, common mode suppression circuitry 106, differential mode artifact suppression circuitry 122, and combiner 124. Note that suppression techniques described herein may be used whether or not delta encoding techniques are used, and whether or not time division multiplexing techniques are used. For example, the common mode suppression circuitry 106 and suppression techniques described herein may be used with or without delta encoder 108 (e.g., a different encoder may be used in other examples), and with or without multiplexer 104 present in the recording channels.

Generally, the common mode suppression circuitry 106 may include circuitry that may sample the voltage on multiple (e.g., two) electrodes of electrodes 102. The common mode suppression circuitry 106 may be arranged to subtract a common mode signal from the pair of electrodes from a subsequent differential input signal received from the electrodes.

Generally, differential mode suppression techniques may include one or more template subtraction methods. The differential mode artifact suppression circuitry 122 may include storage for one or more templates that may represent differential mode artifacts. The combiner 124 may combine (e.g., subtract) the differential mode artifact from the accumulated digital difference signal received from the accumulator 116 and/or register 118. This signal with reduced and/or eliminated differential mode artifacts may be provided to the digital-to-analog converter 120 and converted into an analog signal for use as the analog feedback signal.

All, or a subset, of the components shown in FIG. 1 may be implemented on a chip (e.g., a semiconductor chip and/or substrate). The chip may be implanted in or on tissue (e.g., brain), which may allow for implanted analog front ends for biopotential signal processing and/or implanted recording channels.

Delta encoders and delta encoding techniques described herein may be advantageously used for biopotential signal processing. Biopotential signals may generally have high-frequency, low-amplitude components and large-amplitude, low-frequency components. The high-frequency low-amplitude components generally set a sampling rate to be used by delta encoders described herein (e.g., a sampling rate of the analog-to-digital and/or digital-to-analog converters used may be selected in accordance with the expected high frequency component of the biopotential signal—e.g., at a Nyquist sampling rate with respect to that expected frequency component). The large-amplitude, low-frequency component of the biopotential signal may set a dynamic range of a system (e.g., a dynamic range of one or more amplifiers used may be selected based on the expected amplitude of the biopotential signal). Delta encoders and delta encoding techniques described herein may advantageously allow for processing of the large-amplitude, low-frequency components of biopotential signals and the high-frequency, low-amplitude components. By taking the differences between samples demonstrating these power spectral density (PSD) characteristics, dynamic range requirements may be significantly reduced. Examples described herein may implement digital delta-encoding techniques.

Delta encoders and delta encoding techniques described herein may utilize mixed-signal feedback to shape the signal spectrum. Example delta encoder architectures described herein use delta-encoding to track differences between successive samples with Nyquist rate conversion. This approach may significantly reduce the ADC dynamic range requirement in some examples for signals containing low-amplitude, high-frequency and high-amplitude, low-frequency content.

Figure 2:
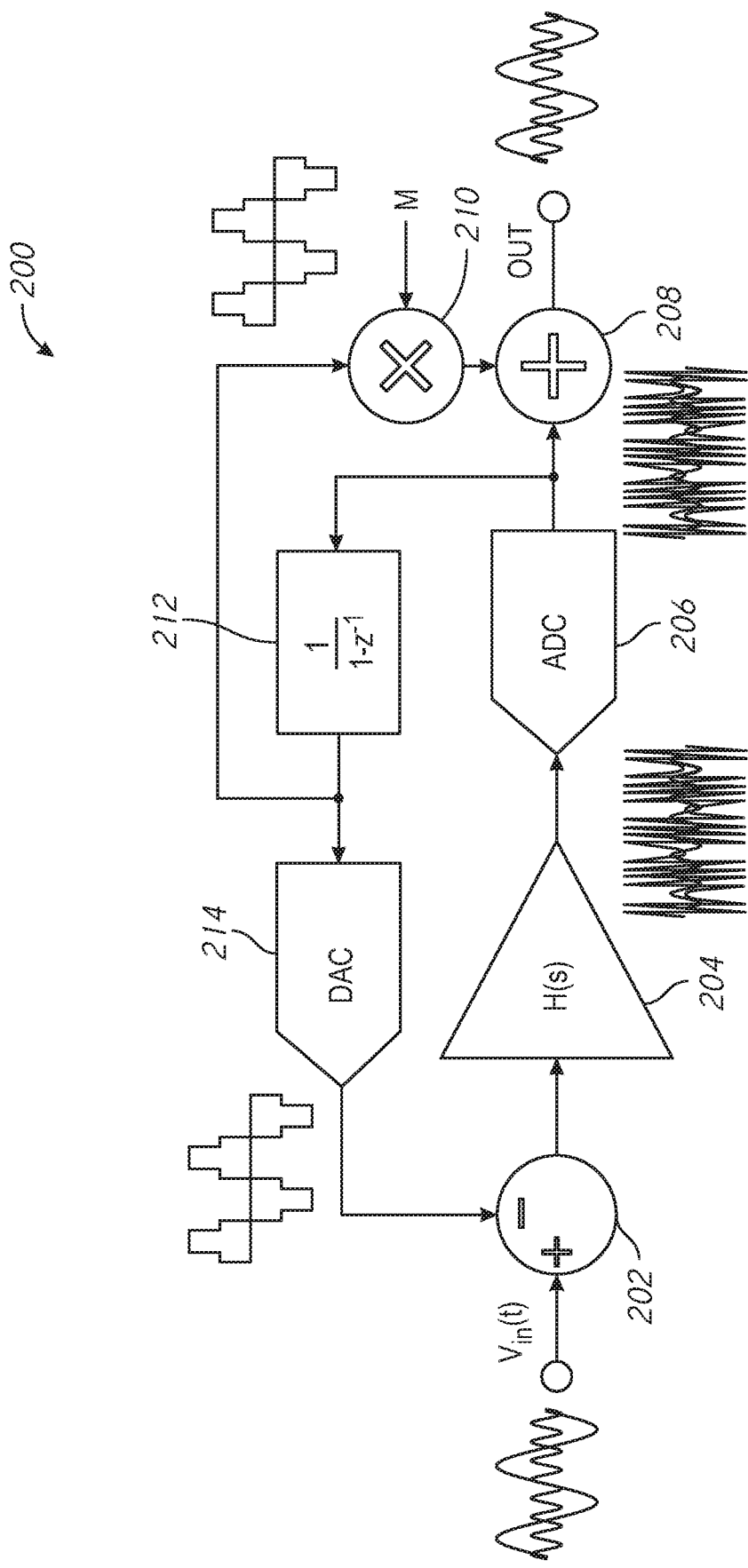
FIG. 2 is a schematic illustration of a delta encoder arranged in accordance with examples described herein.

FIG. 2 is a schematic illustration of a delta encoder arranged in accordance with examples described herein. The delta-encoder 200 includes combiner 202, amplifier 204, analog-to-digital converter 206, combiner 208, multiplier 210, accumulator 212, and digital-to-analog converter 214. Additional, fewer, and/or different components may be used in other examples. In some examples, components may be placed between components shown as connected (e.g., coupled) in FIG. 2. The delta-encoder 200 may be used to implement and/or may be implemented by delta encoders described herein, such as delta encoder 108 of FIG. 1.

The combiner 202 may receive an analog input signal (e.g., from one or more electrodes) and an analog feedback signal (e.g. from digital-to-analog converter 214). The combiner 202 may be implemented using and/or may be used to implement the combiner 110 of FIG. 1 in some examples. The combiner 202 may combine the analog input signal with the analog feedback signal to provide an analog difference signal. The analog input signal may be a biopotential signal.

The combiner 202 may be implemented using an adder in some examples. Other combinations are possible in other examples. The combiner 202 may provide an analog difference signal indicative of the combination of the analog input signal and the analog feedback signal. The analog input signal may be provided at a positive input of the combiner 202 while the analog feedback signal may be provided at a negative input of the combiner 202. Accordingly, in some examples, the combiner 202 may subtract the analog feedback signal from the analog input signal to provide the analog feedback signal.

The analog feedback signal may be a representation of a previous sample. Accordingly, the input signal is differenced by the combiner 202 with the previous sample, and this low-dynamic-range residue may be provided to the amplifier 204 which may provide a certain gain, H(s), to the signal.

Delta encoders described herein may include one or more amplifiers, such as the amplifier 204 of FIG. 2. The amplifier 204 may be implemented using and/or may be used to implement the amplifier 112 of FIG. 1 in some examples. The amplifier 204 may receive an analog difference signal and amplify the analog difference signal to provide an amplified analog difference signal. The amplifier 204 may have a dynamic range which may be less than a dynamic range of the output signal (e.g., output of combiner 208). The amplifier 204 may be implemented using, for example, a low noise amplifier, an operational transconductance amplifier (OTA), a charge-sampling OTA, and/or combinations thereof. Other amplifier configurations may be used in other examples.

Delta encoders described herein may include one or more analog-to-digital converters, such as analog-to-digital converter 206 of FIG. 2. The analog-to-digital converter 206 may be used to implement and/or may be implemented by the analog-to-digital converter 114 of FIG. 1 in some examples. The analog-to-digital converter 206 may convert the amplified analog difference signal into a digital difference signal. Note that the analog-to-digital converter 206 may have a bit resolution less than a bit precision of the digital output signal (e.g., output of combiner 208). The bit resolution of the analog-to-digital converter 206 may have any of a variety of bit resolutions including 4-bit resolution, 8-bit resolution, 16-bit resolution, or other bit resolutions. Generally, as described herein, a bit resolution of the ADC used in delta encoders described herein (e.g., delta-encoder 200) may be less than a bit precision or bit resolution of the output signals provided by the recording channel (e.g., at an output of combiner 208 in FIG. 2).

Note that the analog-to-digital converter 206 may digitize the amplified analog difference signal at a moderate resolution (e.g., 8 bits in some examples). This bit resolution is less than may have been required to digitize the entire analog input signal. The analog-to-digital converter 206 may provide a code to a digital accumulator, e.g., accumulator 212, which may track the large-scale variation of the signal based on the incremental differences between values.

Delta encoders described herein may include one or more accumulators, such as accumulator 212 of FIG. 2. The accumulator 212 may be implemented by and/or used to implement accumulator 116 of FIG. 1 in some examples. The accumulator 212 may accumulate the digital difference signal and provide an accumulated digital difference signal. Generally, the accumulator 212 may track a large-scale variation of the input signal based on incremental changes received from the analog-to-digital converter 206. The accumulator 212 may be implemented using accumulator circuitry.

Delta encoders described herein may include one or more digital-to-analog converters, such as digital-to-analog converter 214 of FIG. 2. The digital-to-analog converter 214 may convert the digital difference signal into the analog feedback signal. Note that, as described herein, the digital-to-analog converter may have a bit resolution less than a bit precision of the digital output signal (e.g., output of the combiner 208). The digital-to-analog converter 214 may be used to implement and/or may be implemented by the digital-to-analog converter 120 of FIG. 1 in some examples. The digital-to-analog converter 214 may be implemented using, for example, a control digital-to-analog converter (CDAC). Other digital-to-analog converter designs may be used in other examples. The digital-to-analog converter 214 may operate at a Nyquist rate. The digital-to-analog converter 214 may have a particular bit resolution, such as a 4-bit resolution, an 8-bit resolution, a 16-bit resolution, or other bit resolutions. Generally, as described herein, a bit resolution of the DAC used in delta encoders described herein (e.g., delta-encoder 200) may be less than a bit precision or bit resolution of the output signals provided by the recording channel (e.g., at an output of combiner 208 of FIG. 2). The bit resolution of the digital-to-analog converter 214 may be the same as a bit resolution of the analog-to-digital converter 206 in some examples. In some examples, the bit resolution of the digital-to-analog converter 214 may be different than the bit resolution of the analog-to-digital converter 206. The bit resolution of both the analog-to-digital converter 206 and the digital-to-analog converter 214 may be less than a bit resolution (e.g., bit precision) of the output signals provided by the recording channel.

For example, the digital-to-analog converter 214 in some examples may have an 8-bit resolution, and the digital-to-analog converter 214 may have an 8-bit resolution while the output signals output from the combiner 208 may have a 14-bit precision (e.g., 14-bit resolution).

Examples of delta encoders described herein may include an output combiner, such as combiner 208 of the delta-encoder 200. The combiner 208 may combine the multiplied accumulated digital difference signal and the digital difference signal to provide a digital output signal. Moreover, examples of delta encoders described herein may include a multiplier such as multiplier 210 of the delta-encoder 200. The combiner 208 and/or multiplier 210 may be used to implement and/or may be implemented by combiner 126 of FIG. 1 in some examples. The combiner 208 may combine (e.g., sum) the digital difference signal provided by analog-to-digital converter 206 with the accumulated digital difference signal provided by the accumulator 212 (which may be weighted by multiplier 210) to provide a digital output signal indicative of the analog input signal. The multiplier 210 may provide a multiplied (e.g., weighted) digital difference signal. Note that a bit precision (e.g., bit resolution) of the output signal may be greater than a bit resolution of the analog-to-digital converter 206 and/or digital-to-analog converter 214. The accumulator 212 may advantageously accumulate successive changes to the input signal such that an output of the accumulator 212 may correspond with a previous value of the input signal, which may boost the bit precision of the output signal. In some examples, the combiner 208 may be used together with multiplier 210 which may be used to weight the accumulated digital difference signal and/or the digital difference signal. Weighting one or both of these signals may compensate for non-idealities in the recording channel, such as nonidealities in the digital-to-analog converter 214.

Note that implementing an encoder with a full-scale feedback DAC may have required oversampling. Instead, in examples described herein, a truncated portion of the ADC may be accumulated and stored as a coarse representation of prior signal (e.g., prior voltage), allowing for a Nyquist-rate feedback capacitive DAC, e.g., digital-to-analog converter 214. The signal may still be fully reconstructed by adding the accumulator 212 output weighted by a gain factor (M) by multiplier 210 to the analog-to-digital converter 206 output. The weights used for the gain factor (M) may be selected, for example, based on a calibration of the digital-to-analog converter 214. Thus, the analog-to-digital converter 206 may act as an interpolator for the delta-encoder 200, allowing high-resolution data acquisition using moderate-resolution converters.

Examples described herein may multiplex feedback networks for many channels using storage in the feedback path. For example, delta encoders may be multiplexed such that the delta encoder may be used to include multiple channels of biopotential input. In Multiplexing techniques described herein may be used to multiplex other feedback networks in other examples. Multiplexing the feedback network may improve a recording channel density.

Figure 3:
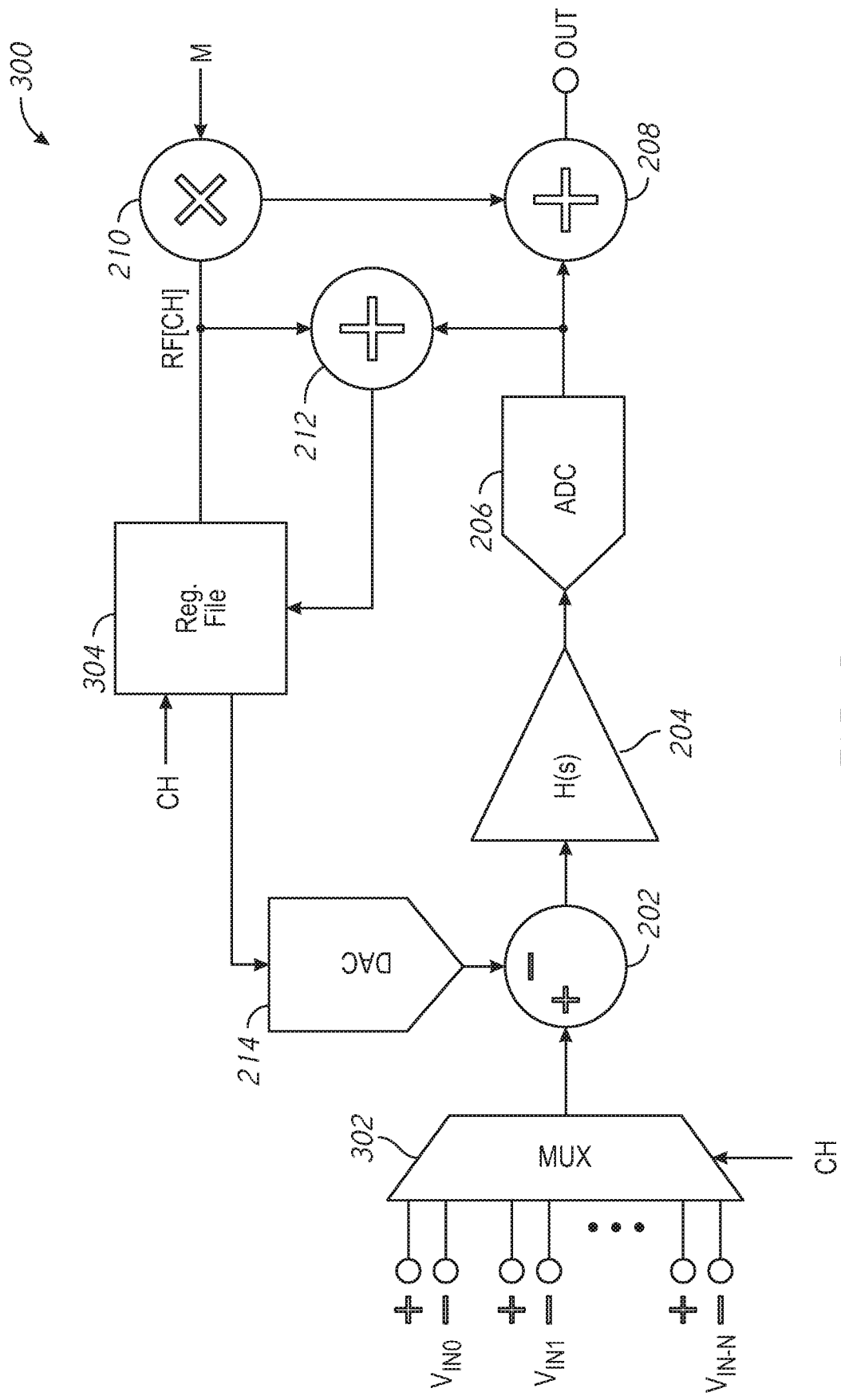
FIG. 3 is a schematic illustration of a delta encoder arranged in accordance with examples described herein.

FIG. 3 is a schematic illustration of a delta encoder arranged in accordance with examples described herein. The delta-encoder 300 includes multiplexing capability. The delta-encoder 300 includes like components with delta-encoder 200 of FIG. 2 utilizing like reference numbers. The delta encoding functionality of the delta-encoder 300 is analogous to that of delta-encoder 200 and is not again described here with reference to FIG. 3. The delta-encoder 300, however, further includes multiplexer 302 and register 304. Accordingly, the delta-encoder 300 may be a multiplexed signal encoder.

The multiplexer 302 may be coupled to a plurality of electrodes (e.g., the electrodes 102 of FIG. 1). The multiplexer 302 may receive input signals from each of the plurality of electrodes (e.g., shown as differential inputs from pairs of electrodes in FIG. 3). The multiplexer 302 may sequentially output analog signals received from each of the plurality of electrodes. For example, differential input signals $V_{IN0} \ldots V_{IN-N}$ are shown as input to multiplexer 302 in FIG. 1. The multiplexer 302 may output these signals sequentially (e.g., $V_{IN0}$, $V_{IN1}$, ... $V_{IN-N}$).

The sequentially output input signals may then be provided to the input of a delta-encoder (e.g., provided to combiner 202). The delta-encoder may, as described herein, encode the analog signals sequentially output from the multiplexer by combining the analog signals with respective feedback signals.

Note that a feedback signal corresponding to a previous version of the same input signal (e.g., from the same electrode(s)) should be used. Accordingly, the delta-encoder 300 may encode the analog signals sequentially output from the multiplexer by combining the analog signals with respective feedback signals which are based on a previous value of the analog signals. Accordingly, the delta-encoder 300 may include register 304 which may store respective previous values of the analog signals. For example, the register 304 may receive accumulated digital difference signals from the accumulator 212 and may store those signals. The register 304 may output an appropriate accumulated difference signal. The register 304 may be implemented using generally any electronic storage including one or more registers, one or more flip-flops, memory, RAM, ROM, or combinations thereof.

The delta-encoder 300 may include a controller (not shown in FIG. 3) which may control the register 304 to output the selected previous values to correspond with the sequentially output analog signals from the multiplexer 302. The controller may be implemented, for example, using one or more processor(s), microcontroller(s), and/or logic circuitry.

Accordingly, the accumulated digital difference signals may be stored on a channel-wise basis and then recalled periodically, providing programmable support for multiple channels (e.g., up to 64 channels in some examples, up to 128 channels in some examples, other numbers of channels in other examples) with a common front-end (e.g., a common delta encoder).

To achieve a large number of multiplexed channels, it may be desirable for amplifier 204 to have a wide bandwidth so that settling is possible between adjacent independent channels. However, such a wide bandwidth may not be desirable as a low-pass response may be desired to eliminate and/or reduce noise aliasing from higher frequencies at the amplifier inputs. To address this, examples described herein may use charge sampling to create a sinc envelope filter on the input signal and input noise, while leaving the amplifier noise of a single stage amplifier in terms of kT/C. Generally, the total noise power due to noise sources before the charge integration stage may be proportional to the sampling interval, which is nominally reduced by a factor of N, the number of independent channels. Therefore, multiplexing generally increases noise voltage due to noise sources before the input of the amplifier by $\sqrt{N}$. Because of this penalty, additional gain stages before the integrating amplifier should be avoided, so that only biological and electrode noise is amplified by this factor.

Crosstalk between adjacent samples of multiplexed channels may also be addressed using examples of systems and techniques described herein. Residual voltage from the previous channel may influence the trajectory and sampled value of the current channel, e.g., when charge sampling, because the signal may not settle. Accordingly, examples described herein may auto-zero one or more nodes of the delta encoder between samples (e.g., an input node, such as an input of combiner 202). The node may be auto-zeroed, for example, by coupling the node to a reference value between samples. For example, a switch may be provided between an input of the combiner 202 and a reference value (e.g., ground). Between samples, a controller may close the switch, allowing the input of the combiner 202 to reach the reference value before opening the switch to allow the input of the combiner 202 to connect to the multiplexer 302 and receive an input signal.

Examples of systems and methods described herein may utilize common mode suppression to eliminate and/or reduce effects of a common mode signal present in one or more biopotential signals collected using systems described herein. Common-mode (CM) artifacts may be on the order of 100 s of mV in some examples, which may degrade performance. Examples described herein may utilize a passive, switched-capacitor technique for CM artifact suppression, which may aid in stabilizing an amplifier operating point, maintaining gain across the input signal range and suppressing distortion by using a correlated-double-sampling technique. During a first sampling phase, the CM signal is extracted by a switched-capacitor network and subtracted from the input signal, canceling it before amplification.

Referring back to FIG. 1, common mode suppression circuitry 106 may be provided in recording channels described herein. The common mode suppression circuitry 106 may utilize a switched capacitor network to sample and store a common mode signal (e.g., a common mode voltage). The common mode signal may be stored, for example, using one or more capacitors. The stored common mode signal may then be used to combine the common mode signal with a differential input signal (e.g., subtract the common mode signal from the differential signal), which may suppress an artifact generated by the common mode signal.

Figure 4:
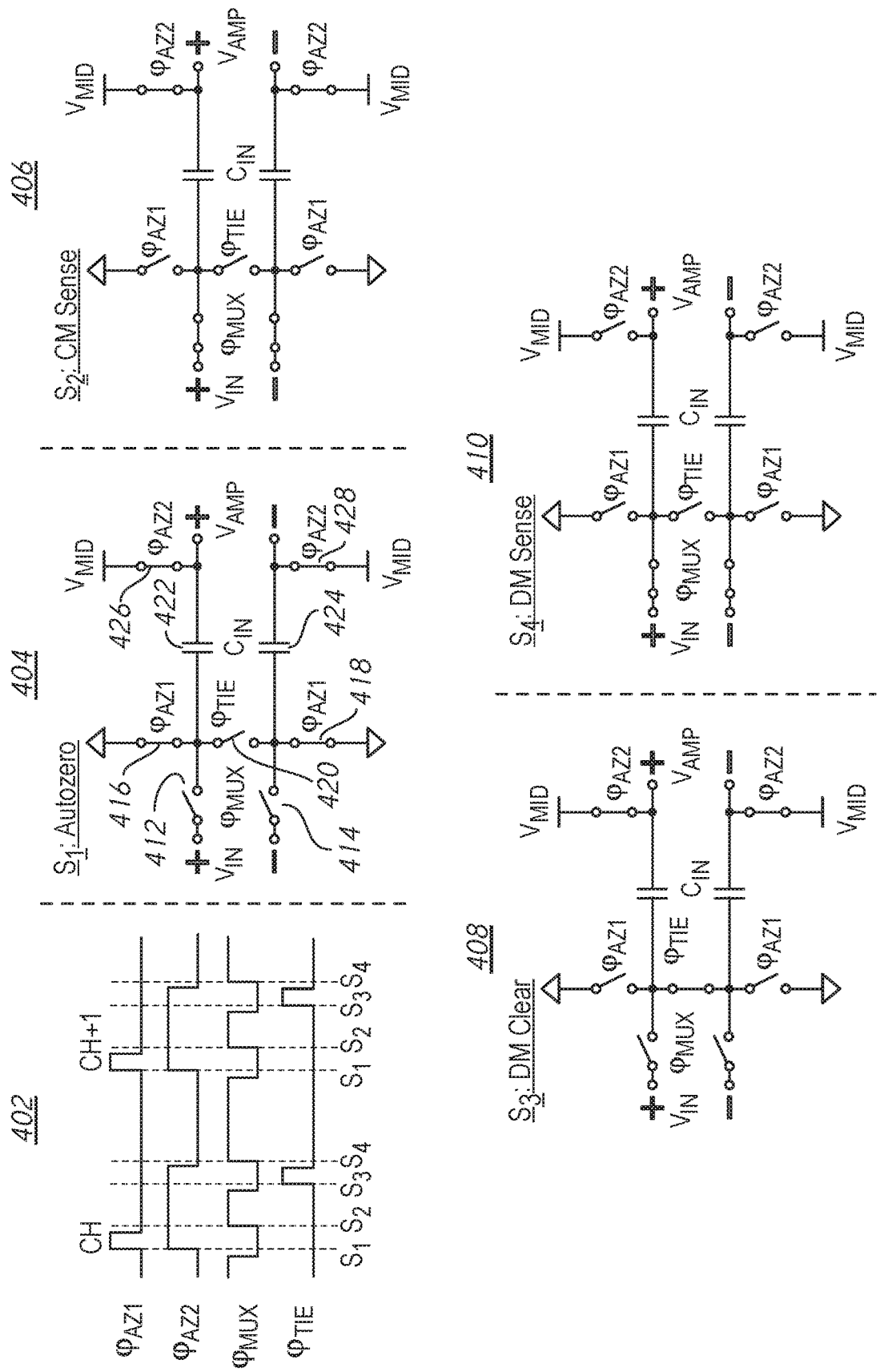
FIG. 4 is a schematic illustration of common mode suppression circuitry and a timing diagram arranged in accordance with examples described herein.

FIG. 4 is a schematic illustration of common mode suppression circuitry and a timing diagram arranged in accordance with examples described herein. FIG. 4 includes timing diagram 402 and schematic illustrations of common mode suppression circuitry during four phases of operation—autozero 404 CM sense 406, DM clear 408, and DM sense 410. The common mode suppression circuitry and phases shown in FIG. 4 may be used to implement common mode suppression circuitry described herein, including common mode suppression circuitry 106 of FIG. 1.

Generally in a first phase (e.g., autozero 404), a switched capacitor network may be auto-zeroed, which may reduce and/or eliminate crosstalk from the previously sampled channel. In a next phase, e.g., CM sense 406, the input signal may be sampled across an input capacitor with a bottom plate at a reference voltage (e.g., grounded). In a next phase, e.g., DM clear 408, the differential-mode component is reduced and/or cleared by connecting the differential inputs. In a next phase, e.g., DM sense 410, the common-mode voltage is stored across the input capacitors, and the bottom plate of the input capacitors is connected to an amplifier (e.g., in a delta encoder) with a reduced and/or eliminated common-mode offset. At this point, the signal can be resampled and the common-mode voltage will not move the capacitor bottom plate (e.g., the amplifier input).

The common mode suppression circuitry of FIG. 4 is arranged to suppress a common mode signal received from a pair of electrodes (e.g., $V_{IN}$ as shown in FIG. 4). Recall, the signal may be received from a multiplexer which may sequentially provide signals from a number of pairs of electrodes, as described herein. The pairs of electrodes may provide biopotential signals as described herein. The common mode suppression circuitry includes a set of input capacitors—capacitor 422 and capacitor 424. The common mode suppression circuitry includes a set of switches—switch 412 and switch 414—each coupled between one side (e.g., an input side) of the input capacitors and the electrodes. The common mode suppression circuitry includes another set of switches—switch 416 and switch 418—coupled between the side (e.g., the input side) of the input capacitors and a reference voltage (e.g., ground as shown in FIG. 4). The common mode suppression circuitry includes switch 420 coupled between the input capacitors (e.g., between the input sides of the capacitors). The common mode suppression circuitry includes another set of switches—switch 426 and switch 428—coupled between another side (e.g., an output side) of the input capacitors and another reference voltage (e.g., $V_{MID}$ as shown in FIG. 4). The output side of the input capacitors may be coupled to an amplifier (e.g., an encoder described herein, such as delta encoder 108 of FIG. 1, delta-encoder 200 of FIG. 2, and/or delta-encoder 300 of FIG. 3).

During operation of the common mode suppression circuitry, the various switches may be controlled by respective control signals as described herein. As shown in FIG. 4, the switch 412 and switch 414 may be controlled by control signal $\varphi_{MUX}$. The switch 416 and switch 418 may be controlled by control signal $\varphi_{AZ1}$. The switch 420 may be controlled by control signal $\varphi_{TIE}$. The switch 426 and switch 428 may be controlled by control signal $\varphi_{AZ2}$. A controller (not shown in FIG. 4) may provide the control signals shown, and may be implemented using one or more processors, microcontrollers, and/or logic circuitry.

The common mode suppression circuitry may have generally four phases of operation, as shown in FIG. 4. Timing diagram 402 illustrates the four phases of operation—$S_1$, $S_2$, $S_3$, and $S_4$. During $S_1$, and autozero phase, the control signals $\varphi_{AZ1}$ and $\varphi_{AZ2}$ may have one state causing closure of their switches (e.g., a high state) while the control signals $\varphi_{MUX}$ and $\varphi_{TIE}$ may have another state causing opening of the associated switches (e.g., a low state). It is to be understood that the high and low states shown herein are selected in accordance with the operation of the switches, and in other examples, the low state of some or all of the control signals may cause closure while a high state may cause opening.

During $S_2$, a common mode (CM) sense phase, the control signals $\varphi_{AZ1}$ and $\varphi_{TIE}$ may have a state causing opening of the associated switches (e.g., a low state), while the control signals $\varphi_{AZ2}$ and $\varphi_{MUX}$ may have a state causing closure of the associated switches (e.g., a high state).

During $S_3$, a differential mode (DM) clear phase, the control signals $\varphi_{AZ1}$ and $\varphi_{MUX}$ may have a state causing opening of the associated switches (e.g., a low state), while the control signals $\varphi_{AZ2}$ and $\varphi_{TIE}$ may have a state causing closure of the associated switches (e.g., a high state).

During $S_4$, a DM sense phase, the control signals $\varphi_{AZ1}$, $\varphi_{AZ2}$, and $\varphi_{TIE}$ may have a state causing opening of the associated switches (e.g., a low state), while the control signal $\varphi_{MUX}$ may have a state causing closure of the associated switches (e.g., a high state).

One phase of operation of common mode suppression circuitry described herein is an autozero phase, such as autozero 404 of FIG. 4. During the autozero phase, the input capacitors may be charged to a reference value. Accordingly, the switch 416 and the switch 418 may be closed, which may couple input sides of the capacitor 422 and capacitor 424 to a reference voltage (e.g., ground in FIG. 4). The switch 426 and switch 428 may be closed, which may couple output sides of the capacitor 422 and capacitor 424 to another reference voltage (e.g., $V_{MID}$) in FIG. 4. The switch 412, switch 414, and switch 420 may be open. Accordingly, a reference voltage (e.g., a difference between $V_{MID}$ and ground) may be applied across capacitor 422 and capacitor 424.

Another phase of operation of common mode suppression circuitry described herein is a CM sense phase, such as CM sense 406 of FIG. 4. During the CM sense phase, the input capacitors may be coupled to a pair of electrodes. For example, the switch 412 and the switch 416 may be closed, which may couple an input side of capacitor 422 and capacitor 424 to a pair of electrodes. The switch 416, switch 418, and switch 420 may be open, disconnecting the input side of capacitor 422 and capacitor 424 from a reference voltage. The switch 426 and switch 428 may be closed, coupling the output side of the capacitor 422 and capacitor 424 to a reference voltage. In this manner, one side of capacitor 422 and capacitor 424 may be placed at a voltage based on a voltage at the electrodes, while another side of capacitor 422 and capacitor 424 is at a reference voltage. In this manner, a voltage indicative of the electrode voltage may be placed across each of capacitor 422 and capacitor 424.

Another phase of operation of common mode suppression circuitry described herein is a DM clear phase, such as DM clear 408 of FIG. 4. In this phase, the capacitor 422 and capacitor 424 may be disconnected from the pair of electrodes. For example, the switch 412 and the switch 414 may be opened, disconnecting an input side of capacitor 422 and capacitor 424 from the input electrodes. In phase DM clear 408, the input capacitors may be coupled together to provide a common mode value on the input capacitors. For example, the switch 420 may be closed, which may couple the input side of capacitor 422 to the input side of capacitor 424. Recall from phase CM sense 406, the capacitors had been charged to a voltage indicative of the voltage on respective electrodes. By tying the capacitors together in phase DM clear 408, both capacitors may be charged to an average of the two capacitor voltages in phase CM sense 406, which may be indicative of a common mode voltage on the input electrodes.

Another phase of operation of common mode suppression circuitry described herein is a DM sense phase, such as DM sense 410 of FIG. 4. In the DM sense phase, pair of electrodes may be coupled to the input capacitors, which may (from phase DM clear 408) have a stored common mode value (e.g., common mode voltage). The output side of the capacitors may accordingly provide a differential output signal having suppressed common mode artifact (e.g., the common mode voltage may be subtracted and/or reduced from the differential input signal). To achieve this, the switch 412 and switch 414 may be closed, which may couple the input sides of capacitor 422 and capacitor 424 to respective differential input electrodes. The switch 416, switch 418, and switch 420 may be open, disconnecting the capacitor 422 and capacitor 424 from one another and the reference voltage. The switch 426 and switch 428 may be open, disconnecting an output side of capacitor 422 and capacitor 424 from a reference voltage, and allowing the differential output signal to be provided to an amplifier and/or encoder. The differential output signal may be encoded using techniques and/or circuitry described herein (e.g., a delta-encoder) to provide a digital output signal.

In examples described herein, time division multiplexing may be used to provide signals from multiple electrodes (e.g., multiple pairs of differential input electrodes) to an amplifier and/or encoder. Accordingly, the common mode suppression circuitry described herein may suppress a common mode signal in each of a plurality of input signals sequentially output from a multiplexer. For example, referring to FIG. 4, the input signal $V_{IN}$ may be provided by a multiplexer (e.g., the multiplexer 104 of FIG. 1 and/or the multiplier 210 of FIG. 2). The multiplexer may sequentially provide differential input signals generated by respective different pairs of differential input electrodes. For each set of input signals, the common mode suppression circuitry may again go through the phases shown in FIG. 4—autozero 404, CM sense 406, DM clear 408, and DM sense 410. The process may be repeated for each multiplexed pair of input electrodes.

Figure 5:
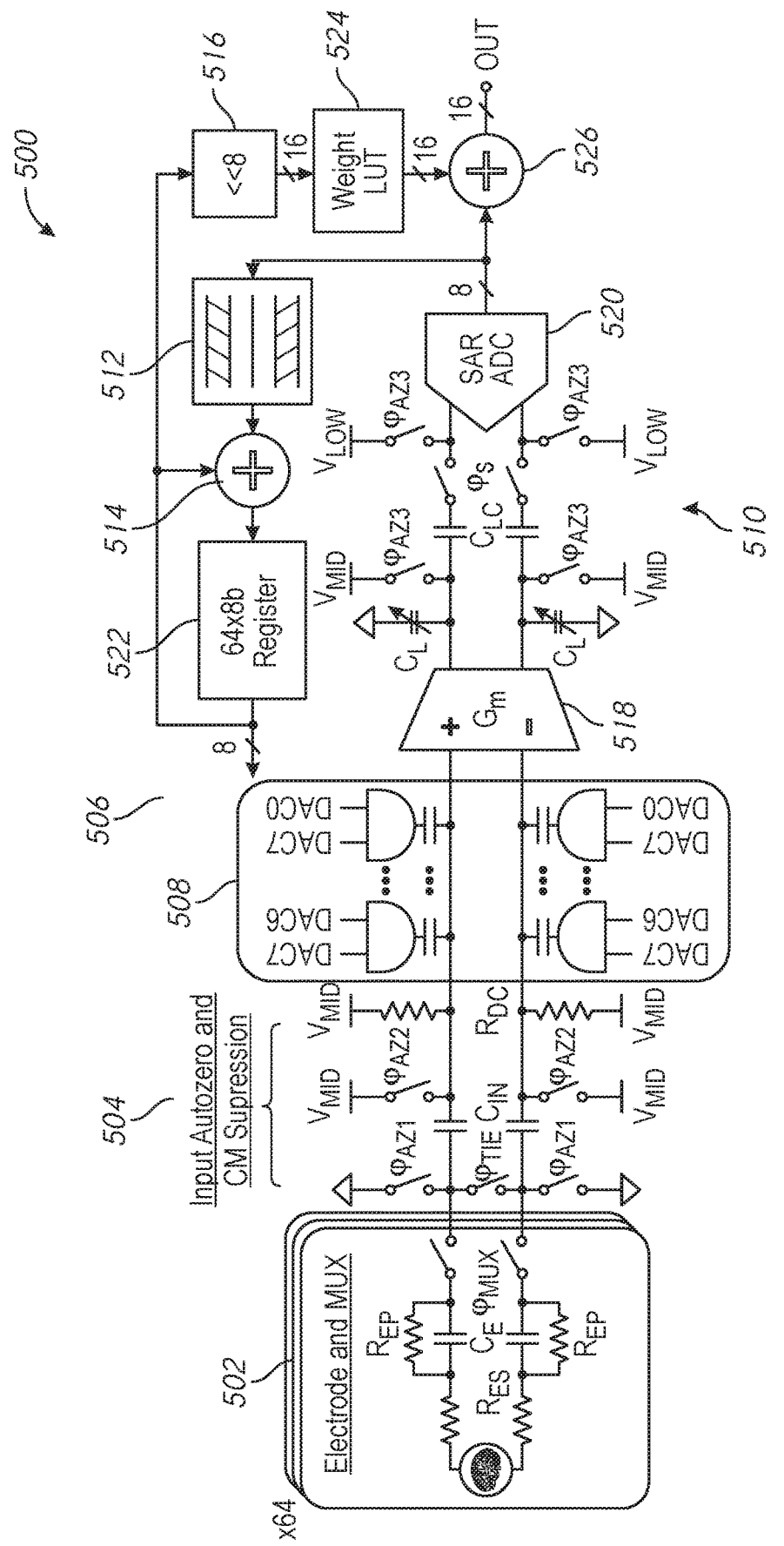
FIG. 5 is a schematic illustration of recording channel(s) arranged in accordance with examples described herein.

FIG. 5 is a schematic illustration of recording channel(s) arranged in accordance with examples described herein. The recording channel(s) 500 include components for performing electrode multiplexing, common mode suppression, and delta encoding as described herein. Note that, in some examples, the components for one or more of these techniques may be removed while retaining the remaining components. The recording channel(s) 500 include electrodes 502 (which may include a multiplexer), CM suppression circuitry 504, and delta-encoder 506. The recording channel(s) 500 may be used to implement, and/or may be implemented by recording channels described herein, such as recording channel(s) 100 of FIG. 1. The electrodes 502 may be implemented using electrodes described herein, such as electrodes 102 of FIG. 1 and/or multiplexer 104 of FIG. 1 and/or multiplier 210 of FIG. 2. The CM suppression circuitry 504 may be used to implement and/or may be implemented by common mode suppression circuitry described herein, such as common mode suppression circuitry 106 of FIG. 1 and/or the common mode suppression circuitry shown in FIG. 4. The delta-encoder 506 may be implemented by and/or used to implement delta encoders described herein, such as delta encoder 108 of FIG. 1, delta-encoder 200 of FIG. 2, and/or delta-encoder 300 of FIG. 3.

The recording channel(s) 500 may implement charge sampling in the amplifier (shown as $G_m$ in FIG. 5), which may reduce and/or eliminate added power requirements of $7\tau$ settling which may otherwise be used to sample the input signal after transitioning to a new channel. Excessive clock jitter can significantly degrade precision in a charge sampling implementation, but the jitter resulting from a ring oscillator powered by a regulated supply may be low enough for desired applications. A return-to-zero technique implemented at the amplifier inputs may reduce and/or eliminate crosstalk between channels and may provide a time-invariant switched-capacitor DC input resistance to each channel. Use of a single amplifier for recording an array of channels naturally may provide correlated double-sampling using a dummy channel to reduce flicker noise if desirable in a particular application.

The electrodes 502 may include electrodes, which may be modeled using the resistances and capacitances shown in FIG. 5—e.g., an input resistance ($R_{ES}$) in series with a parallel combination of another resistance ($R_{EP}$) and an electrode capacitance ($C_E$). As described herein, any number of electrodes may be used, with 64 being illustrated in FIG. 5. A multiplexer may be used to sequentially provide signals from each electrode (and/or pair of differential electrodes). Switches controlled by a control signal $\varphi_{MUX}$ are shown in FIG. 5 and may be used to implement the multiplexer. For example, two switches may be provided for each differential pair of input electrodes. A multiplexer control signal may indicate which pair of differential electrodes is coupled to a next stage of the recording channel at any particular time.

The CM suppression circuitry 504 may include a switched capacitor network and input capacitors, as described, for example, with reference to FIG. 4. CM suppression circuitry 504 may include a pair of input capacitors, $C_{IN}$. CM suppression circuitry 504 may include a pair of switches between the input capacitors and a reference voltage (e.g., ground), which may be controlled by a control signal $\varphi_{AZ1}$. CM suppression circuitry 504 may include a pair of switches between an output plate of the input capacitors and another reference voltage (e.g., $V_{MID}$), which may be controlled by control signal $\varphi_{AZ2}$. An input resistance of the delta-encoder 506 is modeled as resistance $R_{DC}$ in FIG. 5.

The delta-encoder 506 may include DAC 508. The input combiner for the delta-encoder 506 may be implemented using capacitors which couple the DAC 508 to the input signals received from CM suppression circuitry 504. The delta-encoder 506 may include an amplifier 518 coupled to the DAC 508. The DAC 508 may be implemented using a monotonic switching structure similar to ADC 520 described herein. 10 fF unit capacitors may be binary weighted over 7 bits with an additional sign bit from differential operation. The aggregate capacitance of the DAC may form a voltage divider with the 50 pF input capacitors and parasitic capacitance from the amplifier inputs. Driven at a particular voltage (e.g., 2.5V), this voltage divider creates a nominal DAC LSB (e.g., 500 μV). This LSB size covers approximately half of the input-referred differential range of the forward signal path. Variations in the common-mode voltage due to monotonic switching of DAC elements may be at least partially mitigated by inverting the switching direction of the MSB.

The delta-encoder 506 may include sampling circuitry 510 between the amplifier 518 and an ADC 520. The sampling circuitry 510 may be used to sample input signals at a desired time and/or bring the node between the amplifier 518 and the ADC 520 to a reference voltage in between samples to reduce and/or eliminate crosstalk between channels. The sampling circuitry 510 may include a pair of capacitors $C_{LC}$. A pair of switches, controlled by control signal $\varphi_{AZ3}$ may couple an input plate of the capacitors to a reference voltage (e.g., $V_{MID}$ in FIG. 5). Another pair of switches, also controlled by control signal $\varphi_{AZ3}$ (a different control signal may be used in other examples), may be coupled between an input node of the ADC 520 and another reference voltage (e.g., $V_{LOW}$ in FIG. 5). A third pair of switches, controlled by control signal $\varphi_S$, may be coupled between an output plate of the capacitors and an input node of the ADC 520. Through operation of the switches, an input node of the ADC 520 may be coupled to an input signal and/or transitioned to a reference voltage in between samples at desired times.

The ADC 520 may generally serve as the sampling switch and a portion of the load capacitance for the amplifier 518. The ADC 520 may be implemented as a top-plate sampling, monotonic-switching asynchronous SAR ADC. In a fully differential implementation, a 7-bit DAC combined with an initial sign measurement may create an 8-bit output. The capacitor of the sampling circuitry 510 may be implemented using a Metal-Oxide-Metal (MOM) capacitor structure with a unit size of 7.7 fF.

The delta-encoder 506 may include an accumulator, shown in FIG. 5 implemented by thresholding circuitry 512 and combiner 514. The thresholding circuitry 512 may, for example, output an indication of a positive increment (e.g., a+1) for ADC codes (e.g., output of ADC 520) greater than a programmable threshold. The thresholding circuitry 512 may output an indication of a negative increment (e.g., a−1) for ADC codes (e.g., output of ADC 520) less than another programmable threshold. In this manner, input signal samples which are greater or less than a previous sample by threshold amounts may cause an increase and/or decrease to an accumulated signal. The increases and/or decreases may be implemented by combiner 514 and the accumulated signal may be stored, as described herein, in register 522. The accumulated signal may be provided to DAC 508 for conversion to an analog signal used a feedback signal for delta-encoder 506.

The accumulated signal may also be provided to shifter 516, which may shift the signal (e.g., by 8 bits as shown in FIG. 5). The shifted signal may be provided to multiplier 524 for multiplication with a weighting factor (e.g., implemented as a weight look-up table in FIG. 5). The weighted signal may be provided to combiner 526 for combination with the output of ADC 520 to generate an output signal of the delta-encoder 506.

Figure 6:
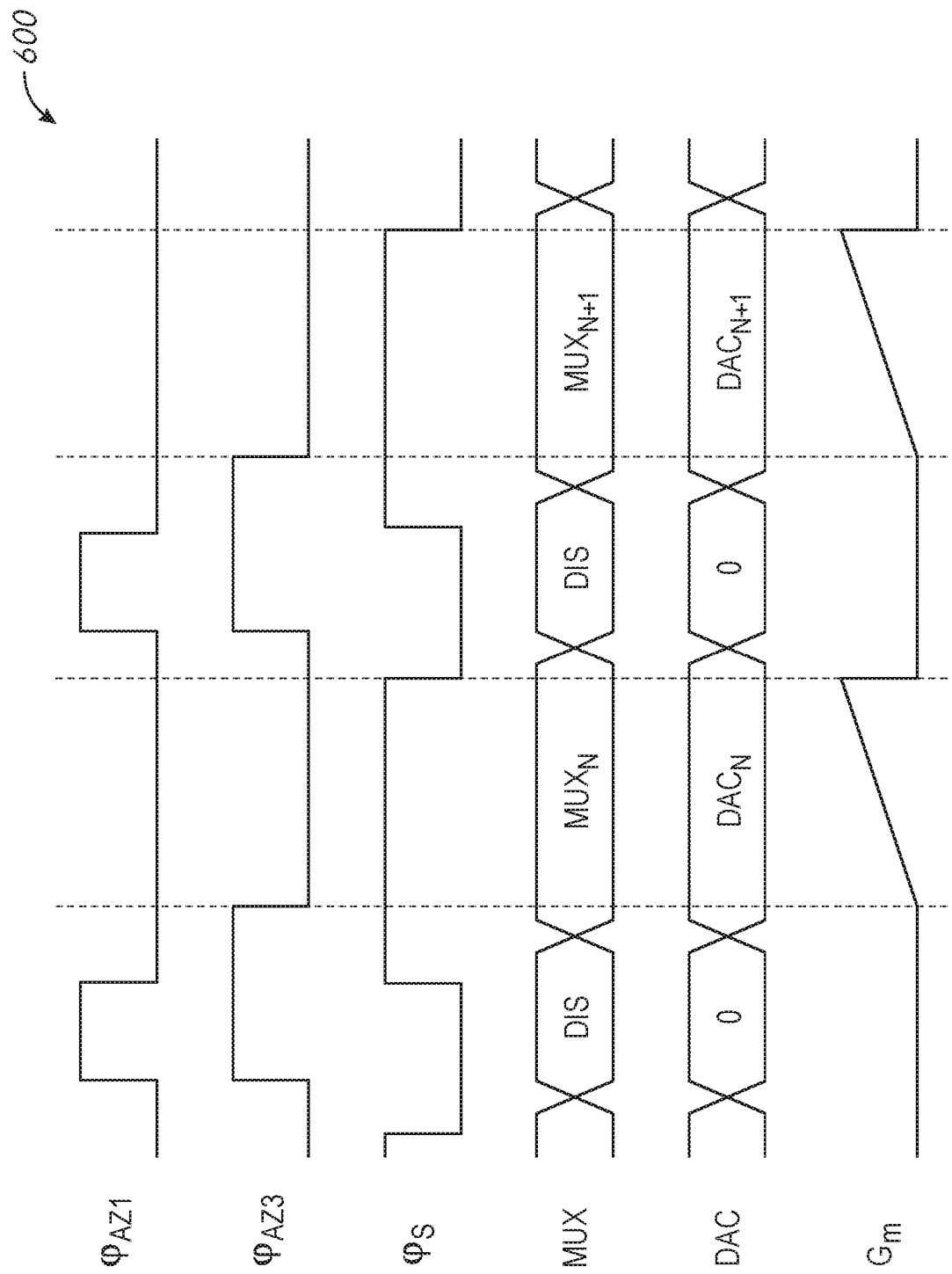
FIG. 6 is a timing diagram for the recording channels of FIG. 5 in accordance with examples described herein.

FIG. 6 is a timing diagram for the recording channels of FIG. 5. The timing diagram 600 is a timing diagram for recording channel(s) 500 in a normal operating mode. Other modes may also be used. The timing diagram 600 illustrates switching control signals $\varphi_{AZ1}$, $\varphi_{AZ3}$, and $\varphi_S$. The timing diagram 600 illustrates multiplexer output MUX (e.g., shown as either disabled, DIS, or providing an input signal $MUX_N$, $MUX_{N+1}$, ... ). The timing diagram 600 illustrates DAC output, DAC (e.g., shown as either 0 or an output $DAC_N$, $DAC_{N+1}$ ... ). The timing diagram 600 illustrates an output of amplifier $G_m$.

When the system is ready to transition to a next channel, the input MUX may be disabled, shown in timing diagram 600 as the DIS portions of multiplexer output MUX. The DAC may then be returned to zero-state, shown as 0 at the DAC output in timing diagram 600. This may aid in ensuring that sampling, amplification and/or quantization for each channel may be performed with identical and/or similar impedances independent of the state of the previous channel.

Next, the auto-zero switches are activated (e.g., $\varphi_{AZ1}$ and $\varphi_{AZ3}$), bringing both the input and output to a known voltage. In nominal operation the amplifier input may not be auto-zeroed, but may utilize a pseudoresistor to set the bias of the amplifier. Using a pseudoresistor may avoid the injection of kT/C noise at the amplifier inputs that may occur with a switch. After the input auto-zero is completed, the auto-zero switch is opened (e.g., control signal $\varphi_{AZ1}$ is transitioned) and the sampling switch at the input to the ADC may be closed (e.g., control signal $\varphi_S$ may transition to close the switch).

At this stage, the recording channel(s) 500 may still not be sampling, because the output auto-zero may still be active (e.g., the control signal $\varphi_{AZ3}$ has not transitioned to close the associated switch). The DAC 508 may then be enabled slightly before the MUX, which may aid in ensuring that the DAC sees a uniform impedance. The auto-zero switch at the output is subsequently opened (e.g., the control signal $\varphi_{AZ3}$ may transition to open the switch), which allows the amplifier 518 to begin accumulating charge at the output. When the sampling window is completed, the sampling switch opens (e.g., the control signal $\varphi_s$ may transition to open the switch) and the whole process begins again on the next channel.

Figure 7:
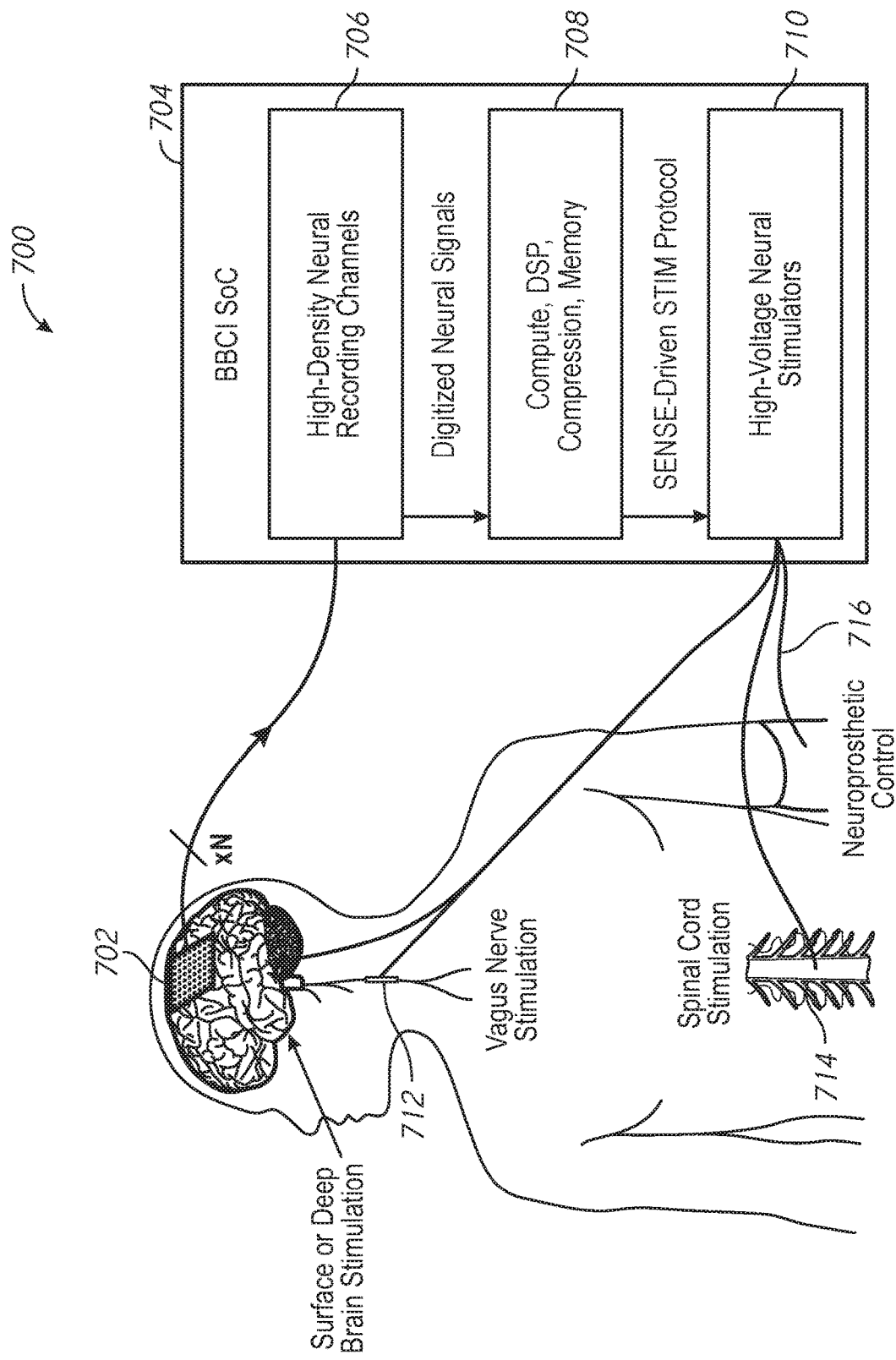
FIG. 7 is a schematic illustration of a BBCI arranged in accordance with examples described herein.

FIG. 7 is a schematic illustration of a BBCI arranged in accordance with examples described herein. The BBCI 700 includes electrodes 702 and system on chip 704. The system on chip 704 may include recording channels 706, signal processing components 708, and/or stimulator(s) 710. The BBCI 700 may include vagus nerve stimulator 712, spinal cord stimulator 714, and/or neuroprosthetic controller 716. The electrodes 702 may be implanted in and/or on a brain. The system on chip 704 may similarly be implanted in and/or on a brain and may be in electronic communication with the electrodes 702. The system on chip 704 may be in electronic communication with a stimulator, such as vagus nerve stimulator 712, spinal cord stimulator 714, and/or neuroprosthetic controller 716. Additional, fewer, and/or different components may be used in other examples.

During operation, bidirectional communication with the brain may be made possible by recording signals emitted by the brain, e.g., using electrodes 702 and system on chip 704, and stimulating tissue either in the cortex or in the peripheral nervous system, e.g., using vagus nerve stimulator 712, spinal cord stimulator 714, and/or neuroprosthetic controller 716. In-line computation elements (e.g., signal processing components 708) may allow for closed-loop bidirectional communication with the central nervous system.

The recording channels 706 may be implemented using examples of recording channels, analog front-ends, and/or signal encoders described herein, including recording channel(s) 100 of FIG. 1 and/or recording channel(s) 500 of FIG. 5. Techniques described herein, including delta encoding, multiplexing, and/or common mode rejection, may be implemented in recording channels 706.

Signals received from neural tissue may be encoded by recording channels and provided to signal processing components 708. The signal processing components 708 may process the neural signals and provide control signals based on the input biopotential signals. The control signals may be used to control one or more stimulator(s) 710. In this manner, a system for stimulation based on input biopotential signals (e.g., neural activity) may be provided.

From the foregoing it will be appreciated that, although specific embodiments have been described herein for purposes of illustration, various modifications may be made while remaining with the scope of the claimed technology.

Examples described herein may refer to various components as "coupled" or signals as being "provided to" or "received from" certain components. It is to be understood that in some examples the components are directly coupled one to another, while in other examples the components are coupled with intervening components disposed between them. Similarly, signal may be provided directly to and/or received directly from the recited components without intervening components, but also may be provided to and/or received from the certain components through intervening components.

What is claimed is:

1. Encoding circuitry comprising:
   a first combiner configured to receive an analog input signal and an analog feedback signal, the first combiner configured to combine the analog input signal with the analog feedback signal to provide an analog difference signal;
   an amplifier configured to receive the analog difference signal and amplify the analog difference signal to provide an amplified analog difference signal;
   an analog-to-digital converter configured to convert the amplified analog difference signal into a digital difference signal;
   an accumulator configured to accumulate the digital difference signal to provide an accumulated digital difference signal;
   a digital-to-analog converter configured to convert the digital difference signal into the analog feedback signal;
   a multiplier configured to provide a multiplied accumulated digital difference signal; and
   a second combiner configured to combine the multiplied accumulated digital difference signal and the digital difference signal to provide a digital output signal.

2. The encoding circuitry of claim 1, wherein the digital-to-analog converter has a bit resolution less than a bit precision of the digital output signal.

3. The encoding circuitry of claim 1, wherein the analog-to-digital converter has a bit resolution less than a bit precision of the digital output signal.

4. The encoding circuitry of claim 1, wherein the digital-to-analog converter and the analog-to-digital converter have bit resolutions less than a bit precision of the digital output signal.

5. The encoding circuitry of claim 4, wherein the digital-to-analog converter and the analog-to-digital converter each have an 8-bit resolution, and wherein the digital output signal has a 14 bit precision.

6. The encoding circuitry of claim 1, wherein a first dynamic range of the amplifier is less than a second dynamic range of the digital output signal.

7. The encoding circuitry of claim 1, wherein the analog input signal comprises a biopotential signal.

8. A multiplexed signal encoder, the multiplexed signal encoder comprising:
   a plurality of electrodes;
   a multiplexer coupled to the plurality of electrodes and configured to sequentially output analog signals received from each of the plurality of electrodes; and
   a delta-encoder coupled to the multiplexer, the delta-encoder configured to encode the analog signals sequentially output from the multiplexer by combining the analog signals with respective feedback signals based on a previous value of the analog signals, wherein the delta-encoder includes:
      a register configured to store respective previous values of the analog signals; and
      a controller configured to output selected previous values from the register to correspond with the sequentially output analog signals.

9. The multiplexed signal encoder of claim 8, wherein the analog signals comprise biopotential signals.

10. The multiplexed signal encoder of claim 8, wherein the delta-encoder includes an amplifier, and wherein the amplifier is configured to amplify analog signals received from each of the plurality of electrodes.

11. The multiplexed signal encoder of claim 8, wherein the delta-encoder comprises:
    a combiner configured to receive the analog signals and respective analog feedback signals, the combiner configured to combine the analog signals with the respective analog feedback signals to provide analog difference signals;
    an amplifier configured to receive the analog difference signals and amplify the analog difference signals to provide amplified analog difference signals;
    an analog-to-digital converter configured to convert the amplified analog difference signals into digital difference signals;
    an accumulator configured to accumulate the digital difference signals to provide accumulated digital difference signals, wherein the register is configured to store the accumulated digital difference signals indicative of the previous values of the analog signals; and
    a digital-to-analog converter configured to convert the digital difference signals into the analog feedback signals.

12. The multiplexed signal encoder of claim 11, wherein the delta-encoder further comprises:
    a multiplier configured to provide multiplied accumulated digital difference signals; and
    another combiner configured to combine the multiplied accumulated digital difference signals and the digital difference signals to provide digital output signals.

13. The multiplexed signal encoder of claim 12, wherein the digital-to-analog converter and the analog-to-digital converter have bit resolutions less than a bit precision of the digital output signals.

14. The multiplexed signal encoder of claim 12, wherein a first dynamic range of the amplifier is less than a second dynamic range of the digital output signals.

* * * * *